United States Patent [19]

Wu

[11] Patent Number: 4,806,660
[45] Date of Patent: Feb. 21, 1989

[54] AURONE OXYPROPANOLAMINES

[75] Inventor: Edwin S. Wu, Rochester, N.Y.

[73] Assignee: Pennwalt Corporation, Philadelphia, Pa.

[21] Appl. No.: 211,116

[22] Filed: Jun. 21, 1988

Related U.S. Application Data

[63] Continuation of Ser. No. 118,385, Nov. 6, 1987, abandoned.

[51] Int. Cl.$^4$ ............................................. C07D 307/83
[52] U.S. Cl. ...................................................... 549/466
[58] Field of Search ......................................... 549/466

[56] References Cited

U.S. PATENT DOCUMENTS

| | | | |
|---|---|---|---|
| 4,391,821 | 7/1983 | Korbonits et al. | 549/406 |
| 4,463,176 | 7/1984 | Dennis et al. | 546/208 |
| 4,495,198 | 1/1985 | Wu | 514/456 |

FOREIGN PATENT DOCUMENTS

| | | |
|---|---|---|
| 79685 | 7/1982 | Romania . |
| 2131688 | 6/1984 | United Kingdom . |

OTHER PUBLICATIONS

Chand, N., "FPL 55712—An Antagonist of Slow Reacting Substance of Anaphylaxis (SRS-A): A Review", *Agents and Actions*, vol. 9, pp. 133–140, 1979.

*Primary Examiner*—Jane T. Fan

[57] ABSTRACT

Compounds such as 6-[3-(cyclopropylamino)-2-hydroxypropoxy]aurone hydrochloride showing inhibitory activity against $LTC_4$-induced contraction of guinea pig ileum are useful as inhibitors of allergic reactions.

4 Claims, No Drawings

AURONE OXYPROPANOLAMINES

This application is a continuation of application Ser. No. 118,385, filed Nov. 6, 1987, now abandoned.

BACKGROUND OF THE INVENTION

Certain new aurones having an oxypropanolamine group at the 6-position and their use for antagonizing the spasmogenic activity of leukotriene $C_4$ ($LTC_4$) in animals are described. In particular, the compounds of the invention are expected to be useful for preventing and treating certain obstructive airways diseases, notably allergic bronchial asthma.

The leukotrienes (LT's) have been identified as the major constituents of SRS-A (slow reacting substance of anaphylaxis). Pharmacological studies indicated that $LTC_4$, $LTD_4$, and $LTE_4$ can induce prolonged contraction of smooth muscle in vitro and in vivo, and are important mediators in the triggering of alleric bronchial asthma.

A widely studied specific antagonist of SRS-A is sodium 7-[3-(4-acetyl-3-hydroxy-2-propylphenoxy)-2-hydroxypropoxy]-4-oxo-8-propyl-4H-1-benzopyran-2-carboxylate (FPL 55712) (Agents and Actions, 9, 133 [1979]).

Aurone derivatives wherein either or both phenyl moiety is unsubstituted or substituted with halogen, alkyl, alkoxy, cycloalkyl, phenyl, $NH_2$, cyano, OH, $NO_2$, alkenyl, $CO_2H$, 5-tetrazolyl or $CH:CHCO_2H$ were claimed to be useful in the treatment of allergies (Romanian Description of the Invention No. 79,685, published July 30, 1982). These compounds do not have the oxypropanolamine side chains which are attached to compounds in the present invention.

Aurone derivatives in which either or both phenyl moiety is unsubstituted or substituted with halogen, alkyl, alkoxy, cycloalkyl, optionally substituted phenyl, haloalkyl, acylamino, carbamoyl, mono- or di-alkylcarbamoyl, amino, mono- or di(alkyl)amino, cyano, hydroxy, nitro, alkenyl, 5-tetrazoyl or carboxyvinyl have been claimed to have antiinflammatory activity (UK Patent Application No. GB 2 131 688 A, published June 27, 1984).

SUMMARY OF THE INVENTION

This invention relates to compounds of the formula (1)

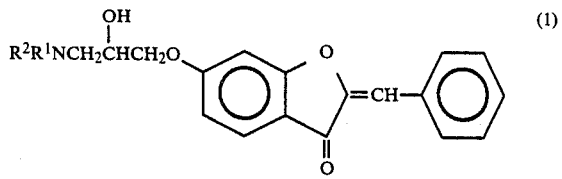

or a pharmaceutically acceptable salt thereof, wherein
R$^1$ is hydrogen or C$_1$–C$_4$ alkyl, and
R$^2$ is C$_1$–C$_4$ alkyl, C$_3$–C$_6$ cycloalkyl, C$_7$–C$_9$ phenylalkyl, or C$_7$–C$_9$ phenylalkyl mono- or disubstituted with a substituent selected from the group consisting of halogen, C$_1$–C$_3$ alkyl, C$_1$–C$_3$ alkoxy and hydroxy.

DETAILED DESCRIPTION OF THE PREFERRED EMBODIMENTS

Synthesis

In general, the auronoxypropanolamines (1) can be prepared from reaction of the epoxide (3) with various amines (4) wherein R$^1$ and R$^2$ are defined as given previously. The epoxide is derived from alkylation of 6-hydroxyaurone (2) with epichlorohydrin.

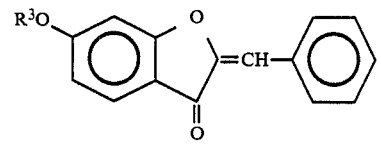

$R^3 = H$     (2)

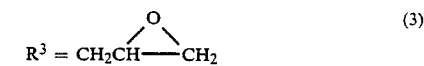

$R^2R^1NH$     (4)

The epoxide (3) can be prepared from reaction of 6-hydroxyaurone with epichlorohydrin in the presence of a base, such as sodium hydroxide or potassium carbonate, and a solvent such as aqueous DMSO, aqueous alcohol (methanol, ethanol, or isopropanol) or acetone at a temperature range of room temperature (RT) to 80° C. The epoxide (3) is then treated with various amines, $R^1R^2NH$, wherein R$^1$ and R$^2$ are defined as given previously, in a solvent such as alcohol (methanol, ethanol, or isopropanol) in a temperature range of 50° C. to 100° C. to give the aminoalcohol (1).

Utility

The compounds disclosed in this invention demonstrate inhibitory activity against $LTC_4$-induced contraction of guinea pig ileum. Therefore, they are expected to be useful as inhibitors of allergic reactions; for example, in the treatment and prophylaxis of bronchial asthma, allergic rhinitis, and/or other allergic diseases.

Test for Inhibition of $LTC_4$-Induced Guinea Pig Ilial Contractions

The evaluation of potential anti-allergic compounds for antagonism of the in vitro effects of $LTC_4$ is conducted according to the following procedure. Guinea pig ilial strips are obtained from recently killed animals and hung in isolated tissue baths comprising a balanced solution of salts such as Krebs' solution. After allowing for one hour equilibration of the tissue in the bath, the gram tension (G.T.) on one tissue is arbitrarily set at one. $LTC_4$ (6 nanomolar concentration) is then added to the tissue bath. This induces a long, sustained contraction of the tissue that is measured on the strip chart recorder (the G.T. increases to about 2). After the $LTC_4$-induced contraction has plateaued and remains stable, increasing amounts of the test compound are added to the bath. If the compound is effective, a decrease in the G.T. (ΔG.T.) from the $LTC_4$-induced value is seen (e.g., from 2 to 1.5). The percent inhibition at each concentration is calculated according to the formula:

$$\left[ \frac{\Delta G.T. \text{ without compound} - \Delta G.T. \text{ with compound}}{\Delta G.T. \text{ without compound}} \right] \times 100\%$$

Four replicate tissues are run.

The results obtained using the title compounds of Examples 1, 2 and 3 as test compounds are given in Table 1.

TABLE 1

| Compound | Percent Inhibition of Contraction at the given Concentration of Test Compound (μMolar) | | | |
|---|---|---|---|---|
| | 1 | 5 | 10 | 50 |
| Example 1 | 16 | 44 | 66 | 135 |
| Example 2 | 23 | 48 | 62 | 154 |
| Example 3 | 25 | 48 | 65 | 144 |

The compounds would normally be mixed with a pharmaceutical carrier if administering to humans, so that the composition contained 0.5 to 20% by weight of the compound.

The compositions are normally adapted for peroral or parenteral use, but may be used in other forms such as suppositories. The peroral compositions are preferably in the form of tablets, capsules or suspensions, while the parenteral composition is preferably an injectable solution or suspension.

Examples of suitable inert pharmaceutical carriers are celluloses (particularly microcrystalline celluloses), sugar syrups, potato starch, talcum, polyethylene glycols and lactose.

Examples of suitable acids for forming the acid addition salts are maleic acid, hydrochloric acid, sulfuric acid, phosphoric acid, methanesulfonic acid, tartaric acid, citric acid, and the cation exchange resins such as the carboxylic acid, phosphonic acid and sulfonic acid resins.

For sustained release, a coated complex of the compound absorbed onto an ion exchange resin may be employed in accordance with the teaching of U.S. Pat. No. 4,221,778 to Y. Raghunathan.

The usual peroral dosage of the compound is 0.1 to 150 mg per day (preferably 0.1 to 50 mg) while the parenteral dosage is normally 0.1 to 40 mg per day (preferably 0.1 to 10 mg).

The capsules, tablets, syrups and suspensions of the compounds are prepared by conventional procedures.

EXAMPLES

The following examples illustrate the invention:

EXAMPLE 1

Preparation of
6-[2-Hydroxy-3-(propylamino)propoxy]aurone Hydrochloride (a) 6-(2,3-Epoxypropoxy)aurone Epichlorohydrin (47.64 g, 0.2 mol) was added to a dark solution of 47.64 g (0.2 mol) of 6-hydroxyaurone (Bull. Chim. Soc. Fr. 3572 [1965]) and sodium hydroxide (8.0 g., 0.2 mol) in 50% aqueous DMSO (400 mL) and was stirred at RT for 2.5 days. An oil formed from the reaction mixture was separated, dissolved in $CH_2Cl_2$ (1:1), washed with water (3×100 mL) and saturated brine (3×100 mL), and dried ($MgSO_4$). The dried solution was combined with the dark brown extract which was obtained by extracting a mixture of the aqueous layer of the reaction mixture and 800 ml of $H_2O$ with $CH_2Cl_2$ (3×500 ml) followed by regular workup as described for the oil. Evaporation of the combined extracts gave a dark brown viscous liquid, 56.5 g (96% yield). This sample was used directly for further reaction. The pure epoxide melted at 110°–111° C. (Ether/$CH_2Cl_2$).

(b) 6-[2-Hydroxy-3-(propylamino)propoxy]aurone Hydrochloride

A dark brown suspension of 6-(2,3-epoxypropoxy)aurone (8.83 g, 40 mmol) and propylamine (10 mL) in abs. ethanol (80 mL) was heated at 60° C. under $N_2$ for 20 hr. The resulting solution was evaporated to give a viscous yellow oil which, upon addition of anhydrous ether, slowly solidified. The solid was dissolved in chloroform (200 mL) and washed with 5% aq. sodium hydroxide to remove 6-hydroxyaurone or other phenolic substances and saturated brine. The dried chloroform solution ($MgSO_4$) was evaporated and the residue obtained was then treated with anhydrous ether to give a brown solid (6.50 g).

The crude free base was purified by column chromatography (silica gel), eluting with 2% MeOH/$CH_2Cl_2$ initially, then with 5% MeOH/$CH_2Cl_2$, and finally with 10% MeOH/$CH_2Cl_2$. This purification gave 3.40 g (24% yield) of a pure free base; mp 140°–142° C. (MeOH/$CH_2Cl_2$).

This pure free base was dissolved in MeOH and treated with HCl saturated EtOH until pH=1. The acidified solution was diluted with anhydrous ether to give a yellow solid (2.84 g) which was recrystallized from i-PrOH-MeOH to afford yellow prisms (1.92 g, 12.3% yield); mp 185°–186° C.

EXAMPLE 2

Preparation of
6-[2-Hydroxy-3-(isopropylamino)propoxy]aurone Hydrochloride

Following the procedure of Example 1(b), reaction of 6-(2,3-epoxypropoxy)aurone with isopropylamine followed by HCl/EtOH gave the title compound, mp 226°–227° C. (i-PrOH-MeOH); 17% yield.

EXAMPLE 3

Preparation of
6-[3-(Cyclopropylamino)-2-hydroxypropoxy]aurone Hydrochloride

Following the procedure of Example 1(b), reaction of 6-(2,3-epoxypropoxy)aurone with cyclopropylamine followed by HCl/EtOH gave the title compound in 61% yield; mp 202°–203° C. (i-PrOH-MeOH).

EXAMPLE 4

Preparation of
6-[2-Hydroxy-3-(phenethylamino)propoxy]aurone Hydrochloride

Following the procedure of Example 1(b), reaction of 6-(2,3-epoxypropoxy)aurone with phenethylamine followed by HCl/EtOH gives the title compound.

EXAMPLE 5

Preparation of
6-[2-Hydroxy-3-(methylphenethylamino)propoxy]aurone Hydrochloride Following the procedure of Example 1(b), reaction of 6-(2,3-epoxypropoxy)aurone with N-methylphenethylamine followed by HCl/EtOH gives the title compound.

EXAMPLE 6

Preparation of 6-[2-Hydroxy-3-[[2-(4-chlorophenyl)ethyl]amino]propoxy]aurone Hydrochloride Following the procedure of Example 1(b), reaction of 6-(2,3-epoxypropoxy)aurone with 2-(4-chlorophenyl)ethylamine followed by HCl/EtOH gives the title compound.

EXAMPLE 7

Preparation of 6-[2-Hydroxy-3-[[2-(4-methoxyphenyl)ethyl]amino]propoxy]aurone Hydrochloride Following the procedure of Example 1(b), reaction of 6-(2,3-epoxypropoxy)aurone with 2-(4-methoxyphenyl)ethylamine followed by HCl/EtOH gives the title compound.

EXAMPLE 8

Preparation of 6-[2-Hydroxy-3-[[2-(3-methylphenyl)ethyl]amino]propoxy]aurone Hydrochloride Following the procedure of Example 1(b), reaction of 6-(2,3-epoxypropoxy)aurone with 2-(3-methylphenyl)ethylamine followed by HCl/EtOH gives the title compound.

EXAMPLE 9

Preparation of 6-[2-Hydroxy-3-[[2-(4-hydroxyphenyl)ethyl]amino]propoxy]aurone Hydrochloride Following the procedure of Example 1(b), reaction of 6-(2,3-epoxypropoxy)aurone with 2-(4-hydroxyphenyl)ethylamine followed by HCl/EtOH gives the title compound.

EXAMPLE 10

Preparation of 6-[2-Hydroxy-3-[[2-(4-chloro-3-methylphenyl)ethyl]amino]propoxy]aurone Hydrochloride Following the procedure of Example 1(b), reaction of 6-(2,3-epoxypropoxy)aurone with 2-(4-chloro-3-methylphenyl)ethylamine followed by HCl/EtOH gives the title compound.

EXAMPLE 11

Preparation of 6-[2-Hydroxy-3-[[2-(3,4-dimethoxyphenyl)ethyl]amino]propoxy]aurone Hydrochloride Following the procedure of Example 1(b), reaction of 6-(2,3-epoxypropoxy)aurone with 2-(3,4-dimethoxyphenyl)ethylamine followed by HCl/EtOH gives the title compound.

EXAMPLE 12

Preparation of 6-[2-Hydroxy-3-[[2-(3,4-dihydroxyphenyl)ethyl]amino]propoxy]aurone Hydrochloride Following the procedure of Example 1(b), reaction of 6-(2,3-epoxypropoxy)aurone with 2-(3,4-dihydroxyphenyl)ethylamine hydrochloride followed by HCl/EtOH gives the title compound.

EXAMPLE 13

Preparation of 6-[2-Hydroxy-3-(dimethylamino)propoxy]aurone Hydrochloride

Following the procedure of Example 1(b), reaction of 6-(2,3-epoxypropoxy)aurone with dimethylamine followed by HCl/EtOH gives the title compound.

What is claimed is:

1. A compound of the formula

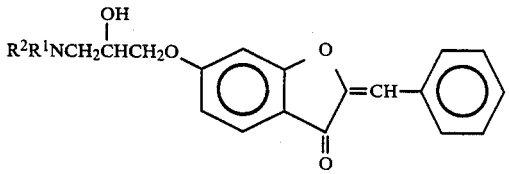

or a pharmaceutically acceptable salt thereof, wherein
$R^1$ is hydrogen or $C_1$–$C_4$ alkyl, and
$R^2$ is $C_1$–$C_4$ alkyl, $C_3$–$C_6$ cycloalkyl, $C_7$–$C_9$ phenylalkyl, or $C_7$–$C_9$ phenylalkyl mono- or disubstituted with a substituent selected from the group consisting of halogen, $C_1$–$C_3$ alkyl, $C_1$–$C_3$ alkoxy and hydroxy.

2. A compound according to claim 1 wherein $R^1$ is hydrogen and $R^2$ is propyl.

3. A compound according to claim 1 wherein $R^1$ is hydrogen and $R^2$ is isopropyl.

4. A compound according to claim 1 wherein $R^1$ is hydrogen and $R^2$ is cyclopropyl.

* * * * *